(12) United States Patent
Guillemin et al.

(10) Patent No.: US 6,680,292 B1
(45) Date of Patent: Jan. 20, 2004

(54) PHARMACEUTICAL COMPOSITION COMPRISING RIBAVIRIN AND GROWTH FACTORS AND METHODS OF USE

(75) Inventors: Roger C. Guillemin, La Jolla, CA (US); Fred Harrison Gage, La Jolla, CA (US); Jasodhara Ray, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/856,100

(22) Filed: Sep. 24, 2001

Related U.S. Application Data (60) Provisional application No. 60/109,308, filed on Nov. 20, 1998, now abandoned.

(51) Int. Cl.$^7$ .................. A61K 31/70; A61K 38/00; A61K 38/24; C07H 19/056; C07H 5/06
(52) U.S. Cl. .............. 514/2; 514/27; 514/43; 514/45; 514/46; 530/397; 530/399
(58) Field of Search .................. 514/2, 27, 43, 514/45, 46, 824, 878, 879; 530/397, 399; 536/28.6, 28.7, 29.1

(56) References Cited

U.S. PATENT DOCUMENTS

| | | |
|---|---|---|
| 4,211,771 A | 7/1980 | Witkowski et al. |
| 4,912,092 A | 3/1990 | Gruber |
| 5,767,097 A | 6/1998 | Tam |

FOREIGN PATENT DOCUMENTS

| | | |
|---|---|---|
| WO | WO 87/05807 | 10/1987 |

OTHER PUBLICATIONS

McAllister and Arciniegas (2002) "Evaluation and Treatment of Postconcussive Symtpoms." NeuroRehabilitation 17(4): 265–283.*

Neet and Campenot (Jul. 2001) "Receptor binding, internalization, and retrograde transport of neurotrophic factors." Cell. Mol. Life Sci. 58(8): 1021–1035.*

Obara and Nakahata (Jun. 2002) "The Signaling Pathway of Neurotrophic Factor Biosynthesis." Drug News Prespect 15(5): 290–298.*

Huang et al. (Mar. 2003) "Etiology of Parkinson's Disease." Can. J. Neurol. Sci. 30(Suppl. 1): S10–S18.*

Kandel et al. (2002) "The Principles of Neural Science" Chapter 43: The Basal Ganglia, pp. 860–866.*

Feign and Zgaljardic (Aug. 2002) "Recent advances in Huntington's disease: implications for experimental therapeutics." Current Opinion in Neurology 15(4): 483–489.*

Yamada and Toshitaka (Sep. 2002) "Therapeutic Approaches to the Treatment of Alzheimer's Disease." Drugs of Today 38(9): 631–637.*

Milicevic et al. (Apr. 15, 2003) "Ribavirin Reduces Clinical Signs and Pathological Changes of Experimental Autoimmune Encephalomyelitis in Dark Agouti Rats." Journal of Neuroscience Research 72(2): 268–278.*

* cited by examiner

*Primary Examiner*—Gary Kunz
*Assistant Examiner*—Christopher James Nichols
(74) *Attorney, Agent, or Firm*—Stephen E. Reiter; Foley & Lardner (57) ABSTRACT

The present invention is directed to compositions comprising 1-(β-D-ribofuranosyl)-1H-1,2,4-triazole compounds and either endogenous or exogenous neurotrophic factors. Methods of using such compounds and compositions are also provided. In one aspect, the invention provides methods of using invention compositions and compounds to enhance neurite outgrowth, neuronal survival and neuronal proliferation in mammalian cells. In a preferred embodiment, a 1-(β-D-ribofuranosyl)1H-1,2,4-triazole compound is infused directly to a desired situs. In a more preferred embodiment the 1-(β-D-ribofuranosyl)-1,2,4-triazole compound is administered orally. In another aspect, the invention provides methods of treating a neurological disease in a mammal subject. In a further aspect, the invention provides methods of treating neuronal trauma in a mammal subject.

20 Claims, 8 Drawing Sheets

PHARMACEUTICAL COMPOSITION COMPRISING RIBAVIRIN AND GROWTH FACTORS AND METHODS OF USE

RELATED APPLICATIONS

This application is a 371 of PCT/US99/27475 (filed Nov. 19, 1999), which in turn claims the benefit of U.S. Provisional Application Serial No. 60/109,308 now abandoned (filed Nov. 20, 1998).

This invention was made with government support under Contract Nos. AG-10435 and NS-6-2348 by the National Institutes of Health. The government has certain rights in the invention.

FIELD OF THE INVENTION

The present invention relates to pharmaceutical compositions and the use thereof in the stimulation of neuronal survival, proliferation and neurite elongation.

BACKGROUND OF THE INVENTION

Fetal cells undergo differentiation and maturation under the influence of many known factors. Fetal cells exposed to various growth factors will differentiate into neuronal cells. Known factors that influence neural growth include Nerve Growth Factor (NGF), Brain-derived growth factor (BDGF), acidic and basic fibroblast growth factor ($\alpha$-FGF and $\beta$-FGF, respectively), and Growth Promoting Factors 2 and 4 ($GPF_2$ and $GPF_4$). Once fully differentiated, neuronal cell survival may be influenced by various conditions and compounds. For example, under adverse conditions such as hypoxia, stroke and the like, factors such as purines released from dead or dying cells, as well as Interleukin-1 (produced by activated microglia), may play a role in neuronal survival and maturation.

In order to study these factors and their role in neuronal development and survival, a number of cell culture systems have been developed. One clonal cell line, termed PC 12, is derived from a rat pheochromocytoma tumor. Pheochromocytoma is a tumor of the adrenal medulla, a neural tissue, that secretes large amounts of adrenaline and noradrenaline. The PC12 cell line is routinely employed in cell culture systems used for the study of neuronal properties.

During the past three decades the number of molecules exhibiting trophic actions in the brain has increased drastically. These molecules promote and/or control proliferation, differentiation, migration, and survival (sometimes even the death) of their target cells. Such factors include neurotrophins, epidermal growth factor, fibroblast growth factor, platelet-derived growth factor, insulin-like growth factors, ciliary neurotrophic factor and related molecules, glial-derived growth factor and related molecules, transforming growth factor-beta and related molecules, neurotransmitters, and hormones. Such factors are characterized by their trophic actions, their expression patterns in the brain, and molecular aspects of their receptors and intracellular signaling pathways. (See, e.g., Weisenhom et al., Int Rev Cytol 1999;189:177–265)

Nerve Growth Factor (NGF) is probably the most extensively studied growth factor. It is known to be involved in many morphological changes such as neurite outgrowth. NGF also helps support the survival of neurons in culture and presumably in vivo also. PC12 cells undergo differentiation into sympathetic neurons when treated with NGF, with about 20 percent of PC12 cells extending neurites in the presence of NGF. NGF also helps support the survival of neurons in culture and presumably in vivo also. NGF is not a ubiquitous neurotrophic factor, however. Within the peripheral nervous system, NGF does not appear to be a survival factor for parasympathetic neurons or developing motor neurons.

Adult neurons normally do not replicate. When cells undergo apoptosis, adenosine nucleosides and nucleotides are released extracellularly with the concentration reaching as high as 1 mM. High adenosine levels effect the development and character of the surrounding cells. One such effect is the stimulation of neurite outgrowth by the surrounding tissue. The ability of purines to stimulate neurite outgrowth in cultured cells has been studied extensively. The results have been mixed, sometimes yielding a positive result, and sometimes yielding a negative result.

Gysbers et al. (Int. J. Dev. Neurosci. 14(1):19–34 (1996)) report that neurite outgrowth of PC12 cells is promoted by the addition of extracellular GTP. Furthermore, GTP together with NGF synergistically enhanced neurite outgrowth. In the same study, the adenine nucleotides ATP, ATP$\gamma$S, ADP$\gamma$S and ADP inhibited, rather than enhanced, NGF-induced neurite outgrowth. Thus, the resultant action of purines on neuronal cells is unclear.

Neary et al. (TINS 19(1):13–18 (1996)) report that the trophic effects of purines on neurons are often synergistic with those induced by polypeptide growth factors. A synergistic enhancement of bFGF-induced neurite elongation was obtained with 2-chloroadenosine in cultured myenteric neuronal cells. No data was reported on whether guanosine enhanced bFGF-induced neurite elongation.

Neary et al. (Neurosci. Letters 242:159–162 (1998)) report that adenosine and ATP have mitogenic activity when added to fetal astrocyte cultures. There was a stimulation of DNA synthesis, and an activation of a mitogen-activated protein kinase termed ERK. However, they did not report any morphological changes in the astrocytes from exposure to adenosine or ATP, nor was the action of guanosine or its related nucleosides and nucleotides reported.

Immunophilins, receptor proteins that bind certain immunosuppressive drugs, have been reported to enhance neurite outgrowth in both PC12 cells and sensory neuronal cultures of dorsal root ganglia when binding ligands that are either immunosuppressive or non-immunosuppressive.

Ribavirin is an antiviral agent that also possesses immunosuppressant activity. However, the neurotrophic activity of Ribavirin and analogs thereof has not been previously recognized.

Thus, in view of the above, it would be advantageous to enhance the ability of growth factors to stimulate neuronal replication, increase neuronal survival, and stimulate growth of neuronal processes by an agent that is amenable to pharmacological manipulation. Furthermore, a non-naturally occurring molecule would be advantageous in order to increase selectivity for neuronal cells and potentially avoid other activities endogenous molecules may possess and thereby decrease the potential for adverse side effects.

SUMMARY OF THE INVENTION

The present invention is directed to compositions comprising 1-($\beta$-D-ribofuiranosyl)-1H-1,2,4-triazole compounds and either endogenous or exogenous neurotrophic factors. Methods of using such compounds and compositions are also provided.

In one aspect, the invention provides methods of using invention compositions nd compounds to enhance neurite outgrowth, neuronal survival and neuronal proliferation in mammalian cells, in vitro and in vivo. In a preferred embodiment, a 1-($\beta$-D-ribofuranosyl)-1H-1,2,4-triazole compound is infused directly to a desired situs. In a more preferred embodiment the 1-($\beta$-D-ribofaranosyl)-1H-1,2,4-triazole compound is administered orally.

In another aspect, the invention provides methods of treating a neurological disease in a mammal subject. In a further aspect, the invention provides methods of treating neuronal trauma in a mammal subject.

BRIEF DESCRIPTION OF THE FIGURES

FIGS. 7A–7D show the effects of Ribavirin in animals with brain lesions tested in a water maze assay relative to naïve controls and brain lesioned animals treated with Cyto C.

FIGS. 8A–8E collectively shows the effects of Ribavirin on neurite growth. FIGS. 8C and 8D show neurite growth in response to Ribavirin compared to control responses (i.e., absence of Ribivirin, FIGS. 8A and 8B). FIG. 8E is a graph showing the effect of Ribavirin on growth cone turning angles compared to controls.

DETAILED DESCRIPTION OF THE INVENTION

In accordance with the present invention, there are provided pharmaceutical compositions comprising:

i) a 1-(β-D-ribofuranosyl)-1H-1,2,4-triazole compound; and ii) optionally, a trophic factor, optionally including a pharmaceutically acceptable carrier therefor.

As used herein the term "1-(β-D-ribofuranosyl)-1H-1,2, 4-triazole compound" refers to compounds having the structure:

wherein R is selected from the group consisting of carboxamide, carboxamidine, and thiocarboxamide; and wherein X is hydrogen, or $C_1$–$C_{18}$ acyl.

Exemplary triazole compounds contemplated by the above generic formula include 1-(β-D-ribofuranosyl)-1H-1, 2,4-triazole-3-carboxamidine, 1-(5'-O-butyryl-β-D-ribofuranosyl)-1H-1,2,4-triazole-3-carboxamide, 1-(5'-O-phosphate-β-D-ribofuranosyl)-1H-1,2,4-triazole-3-carboxamide, 1-(2', 3', 5'-O-acetyl-β-D-ribofuranosyl)-1H-1,2,4-triazole-3 -carboxamide, 1-(β-D-ribofuranosyl)-1H-1, 2,4-triazole-3-carboxamidine, and the like.

As used herein, the term "trophic factor" refers to compounds with trophic actions that promote and/or control proliferation, differentiation, migration, and survival (sometimes even the death) of their target cells. Such factors include neurotrophins, epidermal growth factor, fibroblast growth factor, platelet-derived growth factor, insulin-like growth factors, ciliary neurotrophic factor and related molecules, glial-derived growth factor and related molecules, schwanoma-derived growth factor, glial growth factor, stiatal-derived neuronotrophic factor, platelet-derived growth factor, and scatter factor (HGF-SF), transforming growth factor-beta and related molecules, neurotransmitters, and hormones. Those of skill in the art will readily recognize additional trophic factors which can be employed in the present invention.

As used herein, the term "Neurotrophic factors" refers to trophic factors that promote the survival and functional activity of nerve or glial cells and includes, for example, ciliary neurotrophic factor (CNF), nerve growth factor (NGF), fibroblast growth factor (FGF), brain-derived neurotrophic factor (BDNF), Neurotrophin-3 (NT-3), glia derived neurotrophic factor (GDNF), and the like. Such factors are characterized by their trophic actions, their expression patterns in the brain, and molecular aspects of their receptors and intracellular signaling pathways.

In accordance with another embodiment of the present invention, there are provided methods of enhancing neurite outgrowth, neuronal survival and neuronal proliferation in a mammalian cell, said method comprising administering to said cell an effective amount of a composition as described herein.

In accordance with yet another embodiment of the present invention, there are provided methods of treating a neurological disease (including injuries, dysfunctions and disorders) in a mammal comprising administering a therapeutically effective amount of a composition comprising an effective amount of invention composition as described herein. The present invention concerns the therapeutic application of a composition as described herein to enhance survival of neurons and other neuronal cells in both the central nervous system and the peripheral nervous system. The ability of compositions as described herein to regulate neuronal differentiation and survival during development of the nervous system and also in the adult state indicates that compositions as described herein can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of invention compositions to the treatment of (prevention and/or reduction of the severity of) neurological conditions deriving from injuries, diseases or disorders, including: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system, including Alzheimer's disease; (iii) chronic neurodegenerative diseases of the nervous system, including Parkinson's disease, Huntington's chorea, amylotrophic lateral Isclerosis, and the like, as well as spinocerebellar degenerations; (iv) chronic immunological diseases of the nervous system or affecting the nervous system, including multiple sclerosis; (v) disorders of sensory neurons as well as degenerative diseases of the retina; and the like.

CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function.

Further disease conditions contemplated for treatment in accordance with the invention include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia, astrocytomas, and the like. Further examples of disorders include Alzheimer's disease, Amyotrophic Lateral Sclerosis (ALS) and Parkinson's disease.

Many neurological disorders are associated with degeneration of discrete populations of neuronal elements and may be treatable with a therapeutic regimen which includes compositions as described herein. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. For example, Huntington's disease involves the degeneration of intrastriatal and cortical cholinergic neurons and GABAergic neurons (see, e.g., Hefti et al., Ciba Found Symp. (1996)196:54–69; Koliatsos V. E., Crit Rev Neurobiol (1996) 10(2):205–38). Pick's disease is a severe neuronal degeneration in the neocortex of the frontal and anterior temporal lobes, sometimes accompanied by death of neurons in the striatum. Treatment of patients suffering from such degenerative conditions can include the application of compositions as described herein, in order to manipulate, for example, the de-differentiation and apoptosis of neurons which give rise to loss of neurons. In preferred embodiments, the compositions as described herein are stereotactically provided within or proximate the area of degeneration.

In addition to degenerative-induced dementias, a pharmaceutical preparation of invention compositions can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of invention compositions can be used to treat a restricted form of cerebellar cortical degeneration involving the anterior lobes (vermis and leg areas) such as is common in alcoholic patients.

Other forms of neurological impairment can occur as a result of neural degeneration, such as amyotrophic lateral sclerosis and cerebral palsy, or as a result of CNS trauma, such as stroke and epilepsy. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of invention compositions prevents and/or reverses motor neuron degeneration in ALS patients.

In addition to neurodegenerative diseases, acute brain injuries often result in the loss of neural cells, the inappropriate functioning of the affected brain region, and subsequent behavior abnormalities. Probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis.

The compositions of the present invention can also be used in the treatment of autonomic disorders of the peripheral nervous system, which include disorders affecting the innervation of smooth muscle and endocrine tissue (such as glandular tissue). For instance, invention compositions may be useful to treat tachycardia or atrial cardiac arrythmias which may arise from a degenerative condition of the nerves innervating the striated muscle of the heart.

In addition, invention compositions may be employed to support, or alternatively, antagonize the survival and reprojection of several types of central and peripheral ganglionic neurons, sympathetic and sensory neurons, as well as motor neurons (See, e.g., Terenghi G., J Anat (1999) 194 (Pt 1):1–14). To illustrate, such therapeutic compositions may be useful in treatments designed to rescue, for example, retinal ganglia, inner ear and accoustical nerves, and motoneurons, from lesion-induced death as well as guiding reprojection of these neurons after such damage. Such diseases and conditions include CNS trauma, infarction, infection (such as viral infection with varicella-zoster), metabolic disease, nutritional deficiency, toxic agents (such as cisplatin treatment), and the like. Moreover, certain of the compositions described herein (probably antagonistic forms) may be useful in the selective ablation of sensory neurons, for example, in the treatment of chronic pain syndromes.

Accordingly, there are provided methods of treating neuronal trauma in a mammal comprising administering a therapeutically effective amount of a composition comprising an effective amount of invention composition as described herein. As used herein, the term "Neuronal trauma" refers to any injury to neuronal tissue produced by an exogenous event such as, for example, blunt force or other sudden physical impact that results in neuronal injury or death, either directly or through the abnormal release by dying neurons of toxic levels of endogenous neurotransmitters or metabolites thereof, e.g., glutamate. Neuronal trauma also refers to decreased neurotransmitter production, or a compromise in neuronal function (See, e.g., Fawcett J. W., Spinal Cord (1998) 36(12):811–7).

The compositions of the present invention can also be used in nerve prostheses for the repair of central and peripheral nerve damage. In particular, where a crushed or severed axon is entubulated by use of a prosthetic device, invention compositions can be added to the prosthetic device to increase the rate of growth and regeneration of the dendritic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide which contains invention compositions.

In yet another embodiment, invention compositions can be used in the treatment of neoplastic or hyperplastic transformations, particularly of the central nervous system and lymphatic system. For instance, certain trophic factors are known to have mitotic or apoptotic activity. Thus, certain invention compositions are capable of inducing differentiation of transformed neuronal cells to become post-mitotic or possibly apoptotic. Treatment with certain invention compositions may involve disruption of autocrine loops, such as TGF-beta or PDGF autostimulatory loops, believed to be involved in the neoplastic transformation of several neuronal tumors. Invention compositions may, therefore, be of use in the treatment of, for example, malignant gliomas, medulloblastomas, neuroectodermal tumors, and ependymonas.

Yet another aspect of the present invention concerns the application of the discovery that invention compositions are likely induction signals involved in other vertebrate organogenic pathways in addition to neuronal differentiation as described above, having potential roles in other ectodermal patterning, as well as both mesodermal and endodermal differentiation processes. Thus, it is contemplated that invention compositions can also be utilized for both cell culture and therapeutic methods involving generation and maintenance of non-neuronal tissue, such as in controlling the development and maintenance of tissue from the digestive tract, liver, lungs, and other organs which derive from the primitive gut, as well as dorsal mesoderm-derived structures including muscular-skeletal tissues and connective tissue of the skin; intermediate mesoderm-derived structures, such as the kidney and other renal and urogenital tissues; and head mesenchymal and neural crest-derived tissue, such as cephalic connective tissue and skull and branchial cartilage, occular tissue, muscle and cardiac tissue (see, e.g., Carver and Barness, Clin Perinatol (1996) 23(2): 265–85). This should not be construed as a comprehensive list, and other tissues and diseases that may be affected by the invention compositions are envisaged. For example, memory loss or memory enhancement is encompassed as a potential target for invention compositions (see, e.g., Calamandrei and Alleva Behav Brain Res 1995 Jan 23;66(1–2): 129–32). Those of skill in the art will readily recognize additional applications of invention compositions based on the components of the invention composition, e.g., the activities and, thus, the applications of trophic factors (which have been well characterized and are known to those of skill in the art (Yuen et al., Ann Neurol. (1996) 40(3): 346–54)).

Another aspect of the present invention relates to a method of inducing and/or maintaining a differentiated state, enhancing survival, and/or promoting proliferation of a cell responsive to a composition as described herein, by contacting the cells with invention compositions, with or without trophic factors. For instance, it is contemplated by the invention that, in light of the present finding of an apparently broad involvement of invention compositions, with or without trophic factors, in the formation and maintenance of ordered spatial arrangements of differentiated tissues in vertebrates, the subject method could be used to generate and/or maintain an array of different vertebrate tissue both in vitro and in vivo.

For example, the present method is applicable to cell culture technique. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of trophic factors. In such embodiments of the subject method, the cultured cells can be contacted with invention compositions, with or without trophic factors, to induce neuronal differentiation (e.g. of a stem cell), or to maintain the integrity of a culture of terminally-differentiated neuronal cells by preventing loss of differentiation. The compositions can be administered from a multitude of direct or indirect sources. Such neuronal cultures can be used as convenient assay systems as well as sources of implantable cells for therapeutic treatments, e,g, ex vivo therapy.

To further illustrate potential uses, it is noted that intracerebral grafting has emerged as an additional approach to central nervous system therapies. Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Thus, use of invention compositions for maintenance of neuronal cell cultures can help to provide a source of implantable neuronal tissue. The use of invention compositions in the culture can prevent loss of differentiation, or where fetal tissue is used, especially neuronal stem cells, invention compositions can be used to induce differentiation.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of invention compositions employed in the present method to culture such stem cells can be to induce differentiation of the uncommitted progenitor and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. Invention compositions can be used alone, or can be used in combination with other trophic factors, preferably neurotrophic factors which act to more particularly enhance a particular differentiation fate of the neuronal progenitor cell. In the latter instance, invention compositions might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primitive neuroblasts can be maintained in culture and caused to differentiate with treatment of invention compositions. Exemplary primitive cell cultures comprise cells harvested from the neural plate or neural tube of an embryo even before much overt differentiation has occurred.

The ability of invention compositions to increase, decrease or modify in some other way the number and nature of the stem cell progeny proliferated in the presence of a proliferative factor can be screened on cells proliferated by the present methods. Using these screening methods, it is possible to screen for potential drug side-effects on pre- and post-natal CNS cells by testing for the effects of the biological agents on stem cell and progenitor cell proliferation and on progenitor cell differentiation or the survival and function of differentiated CNS cells. The effects of the biological agents are identified on the basis of significant difference relative to control cultures with respect to criteria such as the ratios of expressed phenotypes (neurons: glial cells, or neurotransmitters or other markers), cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots and PCR can be used to examine the levels of mRNA coding for these molecules, or for enzymes which promote synthesis of these molecules. Alternatively, electrophysiological analysis can be used to determine the effects of biological agents on neuronal characteristics such as resting membrane potential, evoked potentials, direction and ionic nature of current flow and the dynamics of ion channels.

In accordance with a further embodiment of the present invention, there are provided methods of enhancing the activity of endogenous trophic factors in a mammal comprising administering an effective amount of a 1-($\beta$-D-riboftiranosyl)-1H-1,2,4-triazole compound to said mammal. In yet another embodiment of the present invention, the pharmaceutical compound can be administered as part of a combinational therapy with other agents, for example with at least one trophic factor, preferably a neurotrophic factor. Exemplary trophic factors contemplated for use herein include nerve growth factor, cilliary neurotrophic growth factor, schwanoma-derived growth factor, glial growth factor, stiatal-derived neuronotrophic factor, platelet-derived growth factor, scatter factor (HGF-SF), and the like.

Neural stem cells and their progeny can be induced to proliferate and differentiate in vivo by administering to the host, invention composition that will induce proliferation and differentiation of the cells. These compositions include a 1-($\beta$-D-ribofuranosyl)-1H-1,2,4-triazole compound, optionally in the presence of any growth factor known in the art, including the growth factors described above for in vitro proliferation and differentiation. Pharmaceutical compositions include any substance that blocks the inhibitory influence and/or stimulates neural stem cells and stem cell progeny to proliferate and ultimately differentiate. Thus, the techniques described above to proliferate, differentiate, and genetically modify neural stem cells in vitro can be adapted to in vivo techniques, to achieve similar results. Such in vivo manipulation and modification of these cells allows cells lost, due to injury or disease, to be endogenously replaced, thus obviating the need for transplanting foreign cells into a patient. Additionally, the cells can be modified or genetically engineered in vivo so that they express various biological agents useful in the treatment of neurological disorders.

The fact that neural stem cells are located in the tissues lining ventricles of mature brains offers several advantages for the modification and manipulation of these cells in vivo and the ultimate treatment of various neurological diseases, disorders, and injuries that affect different regions of the CNS. Therapy for these can be tailored accordingly so that stem cells surrounding ventricles near the affected region would be manipulated or modified in vivo using the methods described herein. The ventricular system is found in nearly all brain regions and thus allows easier access to the affected areas. If one wants to modify the stem cells in vivo by exposing them to invention compositions, it is relatively easy to implant a device that administers the composition to the ventricle and thus, to the neural stem cells. For example, a cannula attached to an osmotic pump may be used to deliver the composition. Alternatively, the composition may be injected directly into the ventricles. The neural stem cell progeny can migrate into regions that have been damaged as a result of injury or disease. Furthermore, the close proximity of the ventricles to many brain regions would allow for the diffusion of a secreted neurological agent by the stem cells or their progeny.

For treatment of Huntington's Disease, Alzheimer's Disease, Parkinson's Disease, and other neurological disorders affecting primarily the forebrain, growth factors or other neurological agents would be delivered to the ventricles of the forebrain to affect in vivo modification or manipulation of the stem cells. For example, Parkinson's Disease is the result of low levels of dopamine in the brain, particularly the striatum. It would be advantageous to induce a patient's own quiescent stem cells to begin to divide in vivo and to induce the progeny of these cells to differentiate into dopaminergic cells in the affected region of the striatum, thus locally raising the levels of dopamine.

The active components described for use herein can be delivered in a suitable vehicle, thereby rendering such compositions amenable to oral delivery, transdermal delivery, subcutaneous or intravascular delivery (e.g., intravenous delivery, intramuscular delivery, intraarterial delivery, intraperitoneal delivery, and the like), intracranial, topical delivery, inhalation delivery, osmotic pump, and the like. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir. Preferably, invention compositions can be administered in any manner known in the art in which the subject compositions may either pass through or by-pass the blood-brain barrier. Methods for allowing factors to pass through the blood-brain barrier include minimizing the size of the factor, or providing hydrophobic factors which may pass through more easily.

Depending on the mode of delivery employed, invention compositions can be delivered in a variety of pharmaceutically acceptable forms. For example, invention compositions can be delivered in the form of a solid, solution, emulsion, dispersion, micelle, liposome, and the like.

Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. The active compounds contemplated for use herein are included in the pharmaceutical composition in an amount sufficient to produce the desired effect upon the target process, condition or disease.

Pharmaceutical compositions containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions. In addition, such compositions may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. Tablets, and the like, may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical compositions may also be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, water, buffered saline, polyol (for example, glycerol, propylene glycol, liquid polyethylene glycol and the like) or suitable mixtures thereof or the like. Buffers, preservatives, antioxidants, and the like, can be incorporated as required.

Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In addition, sustained release systems, including semipermeable polymer matrices in the form of shaped articles (e.g., films or microcapsules) can also be used for the administration of the active compound employed herein. Rechargable or biodegradable devices may also provide methods of introduction, particularly where gradients of concentrations in a tissue are desired. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an invention composition at a particular target site. The generation of such implants is generally known in the art.

Direct delivery of compounds and pharmaceutical compositions to the brain of patient may be desired for the treatment of patients with neurological diseases or conditions affecting the brain. To effect this mode of administration, a silicon catheter can be surgically introduced into a ventricle of the brain of a human patient, and can be connected to a subcutaneous infusion pump (Medtronic Inc., Minneapolis, Minn.) that has been surgically implanted in the abdominal region (Zimn et al., Cancer Research, 1984, 44, 1698; Shaw, Cancer, 1993, 72(11 Suppl.), 3416). The pump is used to inject the compounds or pharmaceutical compositions and allows precise dosage adjustments and variation in dosage schedules with the aid of an external programming device. Infusion rates may range from 0.1 mL/h to 1mL/h. Depending on the frequency of administration, ranging from daily to monthly, and the dose of drug to be administered, ranging from 0.01 $\mu$g to 100 g per kg of body weight, the pump reservoir may be refilled at 3–10 week intervals. Refilling of the pump is accomplished by percutaneous puncture of the self-sealing septum of the pump.

Introduction of a drug into the spinal column of a patient may be desired for the treatment of patients with diseases of the central nervous system. To effect this route of drug administration, a silicon catheter can be surgically implanted into the L3–4 lumbar spinal interspace of a human patient, and is connected to a subcutaneous infusion pump which has been surgically implanted in the upper abdominal region (Luer and Hatton, The Annals of Pharmacotherapy, 1993, 27, 912; Ettinger et al., 1978, Cancer, 41, 1270,1978; Yaida et al., Regul. Pept., 1995, 59, 193). The pump is used to inject the compounds or pharmaceutical compositions and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 $\mu$g to 100 g per kg of body weight, the pump reservoir may be refilled at 3–10 week intervals. Refilling of the pump is accomplished by a single percutaneous puncture to the self-sealing septum of the pump. The distribution, stability and pharmacokinetics of oligonucleotides within the central nervous system may be followed according to known methods (Whitesell et al., Proc. Natl. Acad. Sci. (USA), 1993, 90, 4665).

To effect delivery of compounds and pharmaceutical compositions to areas other than the brain or spinal column via this infusion pump method, the silicon catheter is configured to connect the subcutaneous infusion pump to, e.g., the hepatic artery, for delivery to the liver (Kemeny et al., Cancer, 1993, 71, 1964). Infusion pumps may also be used to effect systemic delivery of compounds and pharmaceutical compositions (Ewel et al., Cancer Research, 1992, 52, 3005; Rubenstein et al., J. Surg. Oncol., 1996, 62, 194).

Since individual subjects may present a wide variation in severity of symptoms and each active ingredient has its unique therapeutic characteristics, it is up to the practitioner to determine a subject's response to treatment and vary the dosages accordingly. For example, effective levels of the invention compositions for a given patient can readily be achieved by monitoring the patient using commonly available techniques, such as, for example, by subjecting serum obtained from the patient to high performance liquid chromatography (HPLC). The practitioner can then determine whether increased or decreased dosages of the invention compositions are indicated, based on the level detected in the patient's serum.

Typical daily doses of the active component, in general, lie within the range of from about 1.0 ng up to about 100 mg per kg body weight, and, preferably within the range of from about 1.0 ng up to about 5 mg per kg body weight and, more preferably within the range of from about 10 ng up to about 0.4 mg per kg body weight. Daily doses can be administered up to four times daily. The daily dose lies within the range of from about 1.0 ng to about 100 mg per kg body weight, and, preferably, within the range of from 10 ng to 10 mg per kg body weight, and more preferably, within the range of from 10 ng to about 1 mg per kg body weight. Where one will operate within the above ranges will vary based on a variety of considerations, such as, for example, the age of the patient, the size of the patient, what other medications, if any, the patient may be taking (especially steroids), and the like.

As readily recognized by those of skill in the art, the active compounds contemplated for use herein can be administered as part of a slow release formulation, as a single bolus for rapid administration, as part of a depot formulation, as part of a nutritional supplement, and the like.

In order to further illustrate the present invention and advantages thereof, the following specific examples are given, it being understood that the same are intended only as illustrative and in nowise limitative.

EXAMPLE 1

Tissue Culture

PC12 cells were maintained in RPMI-1640 medium supplemented with 5% fetal calf serum (FCS), 5% heat-inactivated horse serum (HS), 100 units/ml penicillin G sodium, 100 $\mu$g/ml streptomycin sulfate and 0.245 $\mu$g/ml amphotericin B. NGF-treated cells were grown in the presence of 500 pg/ml mouse 2.5S NGF. The 1-($\beta$-D-ribofuranosyl)-1H-1,2,4-triazole-3-carboxamide was supplied by ICN Pharmaceuticals. HCN cells were maintained in serum-free N2 basal media with 500 pg/ml of FGF-2. Cells were plated on plastic tissue culture plates coated with polyornithine.

EXAMPLE 2

Neurite Outgrowth Measurements

Neurite outgrowth was determined by measuring neurites from the cell body to the longest point and by counting the number of neurites per cell according to the method of Gysbers et al. (Gysbers et al., NeuroReport 3:997–1000 (1992) and Gysbers et al., Int. J. Dev. Neurosci. 14:19–34 (1996)). Cells are stained with antibodies for Rip, Glial Fibrillary Acidic Protein (GFAP), Microtubule Associated Protein 2ab (MAP2ab), and Calbindin (a Ca-buffering protein).

Briefly, cells were plated on poly-DL-ornithine-coated wells in 24-well plates at a concentration of $2.5\times10^4$ cells per well in RPMI-1640 medium containing 1.5% FCS, and 1.5% HS. Test compounds and NGF were added immediately after plating. After 48 hours the medium was gently aspirated and the cells were fixed in 10% formalin in normal saline. The number of cells bearing neurites greater than one cell body diameter after each treatment with test compound was divided by the total number of cells counted.

The ratio of the number of cells bearing neurites in each treatment were divided by the total number of cells counted per treatment to determine the proportion of neurite bearing cells for each sample. The mean values ($\pm$S.E.M.) were then calculated for each treatment. The effects of the various test compounds plus NGF on neurite outgrowth were compared to that with NGF alone by two way analysis of variance (ANOVA). The effect of the test compounds plus NGF is expressed as a percentage of the values obtained using 500 pg/ml NGF (which is given an arbitrary * value of 100% since neurite outgrowth proportions varied between experiments, usually from 20 to 35% for NGF-alone treatments). The average number of neurites per cell and branches per neurite were determined from representative photographs of the cells under the various treatments.

EXAMPLE 3

Transfection of Fibroblasts

Retroviral vectors for transduction of primary rat fibroblasts were prepared as previously described (Tuszynski et al., Exp. Neurol. 137:157–173 (1996)). Briefly, the cDNA for the prepro-form of NGF was placed into a modified Maloney murine leukemia virus; this gene was constitutively expressed by the viral 5 long terminal repeat promoter. Plasmids were introduced into the ecotropic producer cell line Psi-2 by calcium phosphate transfection. Supernatants from Psi-2 cells were used to infect the amphotropic PA317 cell line, G418-resistant clones that expressed full-length recombinant protein were identified. Viral titers of $10^6$–$10^7$ cfu were obtained (Tuszynski et al., Exp. Neurol. 137:157–173 (1996)). In vitro production of NGF from infected fibroblasts was determined using a two-site enzyme-linked immunoassay sensitive to 5 pg/ml. The enzyme assay is described in Tuszynski et al., Exp. Neurol. 126:1–14 (1994).

Expression of neurotrophic factors in situ requires the following steps: construction of an expression vector, choice of host cell line, introduction of the expression vector into host cells, and manipulation of recombinant host cells to increase expression levels of the neurotrophic factor in a mammalian host and implantation of transformed cells into a subject.

Expression vectors for use in animal cells can be of several types including, for example, strong constitutive expression constructs, and inducible gene constructs. In all cases, promoters and other gene regulatory regions such as enhancers (inducible or not) and polyadenylation signals are placed in the appropriate location in relation to the desired neurotrophic factor cDNA sequences in plasmid-based vectors.

A number of different cell lines can be used to express the desired neurotrophic factor and assess the potential for expression, however, the preferred cell is the human fibroblast with a selection marker.

Vectors containing the desired cDNA can be introduced into the selected cell line using any of a number of gene-transfer techniques. Such methods include, for example, calcium phosphate-DNA precipitation, liposomes, and electroporation.

Cells that express the desired neurotrophic factor can be grown under conditions that will increase the level of expression. Cells positively selected for the desired gene product are then available for implantation into the host mammal, preferably a human subject.

Cells may be implanted either in the central nervous system or the peripheral nervous system. Methods well known in the art may be used to implant the cells at the desired situs, such as, for example, the spinal chord, the thalamus, the substantia nigra, and the like.

Fibroblasts transfected as described above are implanted in a desired situs within the nervous system at sufficient number so as to be therapeutically effective.

As previously reported, NGF-transduced fibroblasts expressed human NGF mRNA and produced 4.8 ng human NGF protein/$10^6$ cells/day, whereas fibroblasts transduced with the reporter gene $\beta$-gal and uninfected fibroblasts produced no detectable hNGF. Previously it has been reported that grafts of hNGF-transduced fibroblasts produce 13.4 ng/g human NGF 3 months after in vivo grafting (Grill et al., Exp. Neuro. 148:444–452 (1997)), indicating sustained in vivo transgene expression throughout the duration of the experiment.

Both NGF-producing grafts and control grafts survived throughout the postgrafting period. Integration of both graft types into host spinal cord was observable in Nissl-stained sections.

EXAMPLE 4

In Vitro Stimulation of Neurons by Ribavirin

Two neuronal and two non-neuronal cell lines were tested to assess the ability of Ribavirin to enhance neurite outgrowth, cell survival and proliferation.

Effect of Ribavirin on PC-12 Cells

PC12 cells were grown as described above and plated at a density of 10,000 cells/well in RPMI with 500 pg/ml NGF. Ribavirin was added at various concentrations on day 0. Cells were counted and neurite elongation evaluated on days 0, 1 and 3. The media was not changed for the duration of the experiment.

Figure 1:
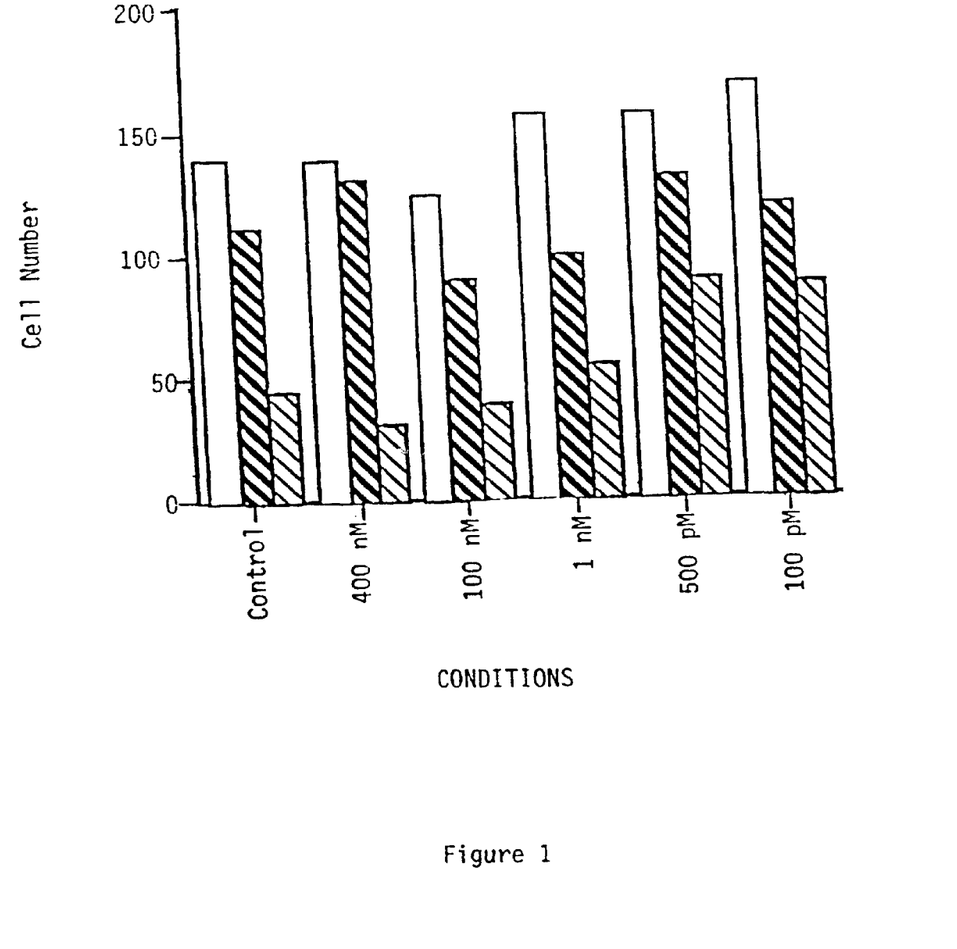
FIG. 1 is a graph of the effects of Ribavirin on PC12 cells in the absence of NGF. Cell numbers on Day 0 are represented by open boxes; cell numbers on Day 1 are represented by darkly hetched boxes; and cell numbers on Day 3 are represented by lightly hatched boxes.

FIG. 1 is a graph depicting the effect of various concentrations of Ribavirin in the absence of NGF. No statistically significant effect on cell survival or proliferation was observed.

Figure 2:
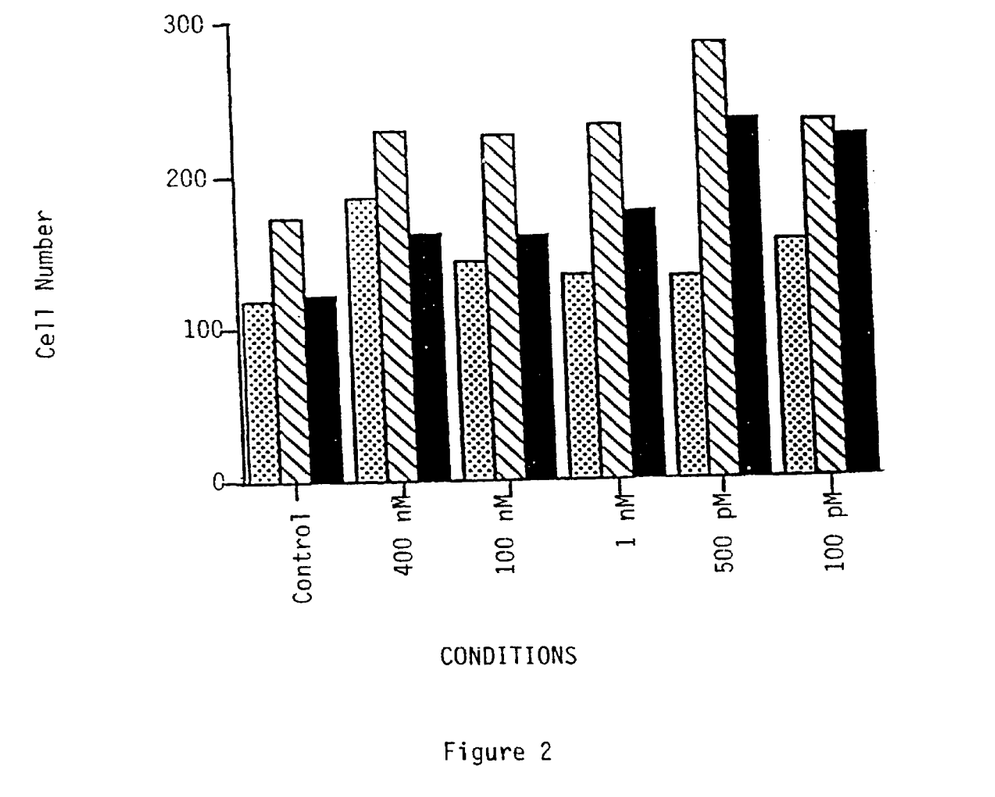
FIG. 2 is a graph of the effects of Ribavirin on PC 12 cells in the presence of NGF. Cell numbers on Day 0 are represented by spotted boxes; cell numbers on Day 1 are represented by hatched boxes; and cell numbers on Day 3 are represented by blackened boxes.

As can be seen from FIG. 2, Ribavirin augmented/enhanced the effects of NGF on the survival and proliferation of PC12 cells as assessed at day 1 and day 3, respectively. Additionally, neurite elongation and networking was enhanced at all concentrations tested (100 pM, 500 pM, 1 nM, 100 nM and 400 nM).

Effect of Ribavirin on HCN Cells

Figure 3:
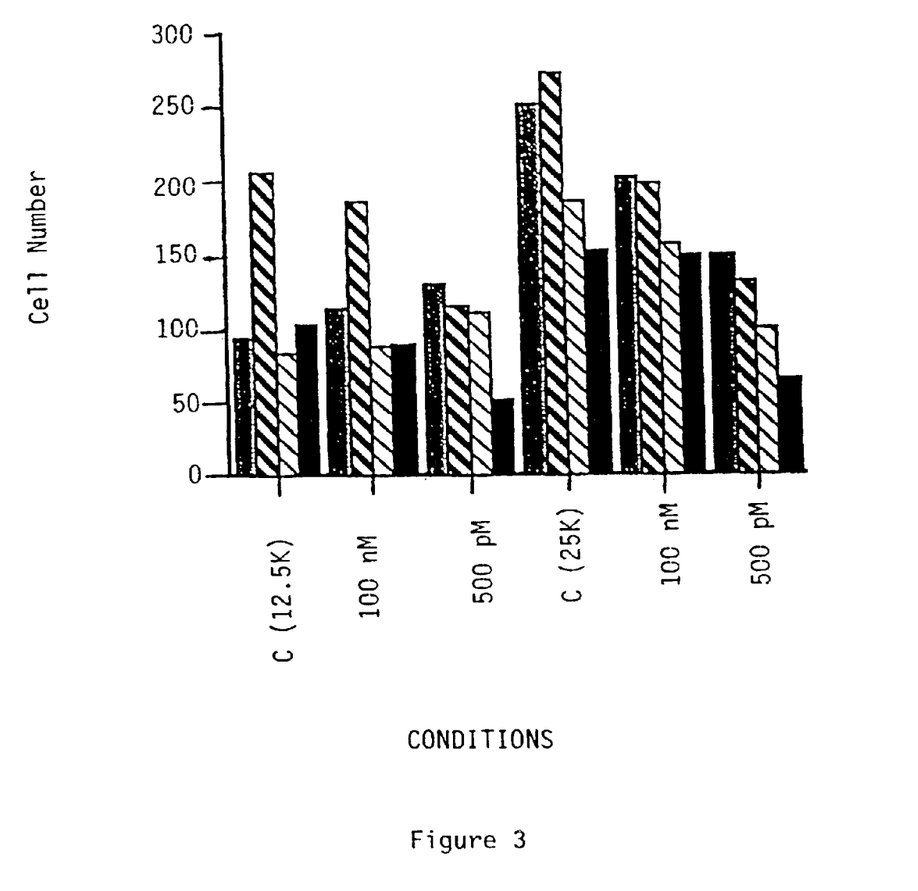
FIG. 3 is a graph of the effects of Ribavirin on HCN cells (at plating density of 12,500 or 25,000 cells/well) in the absence of FGF-2. Cell numbers on Day 0 are represented by shaded boxes; cell numbers on Day 1are represented by darkly hatched boxes; cell numbers on Day 3 are represented by lightly hatched boxes; and cell numbers on Day 5 are represented by blackened boxes.

Experiments on HCN cells were performed under conditions similar to those described above for PC12 cells, except FGF-2 was used instead of NGF. Cells were plated at a density of either 12,500 cells/well or 25,000 cells/well. Ribavirin alone had no effect on cell survival or proliferation at either cell density or Ribavirin concentration tested (FIG. 3).

Figure 4:
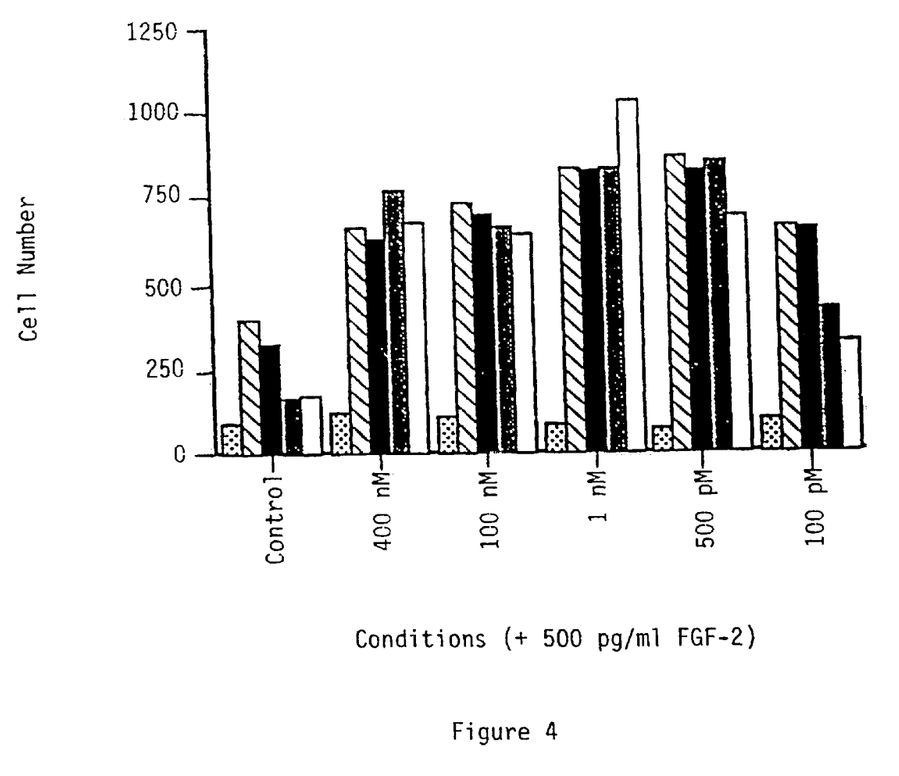
FIG. 4 is a graph of the effects of Ribavirin on HCN cells (at plating density of 12,500 cells/well) in the presence of FGF-2. Cell numbers on Day 0 are represented by spotted boxes; cell numbers on Day 1are represented by hatched boxes; cell numbers on Day 3 are represented by blackened boxes; cell numbers on Day 5 are represented by shaded boxes; and cell numbers on Day 7 are represented by open boxes.
Figure 5:
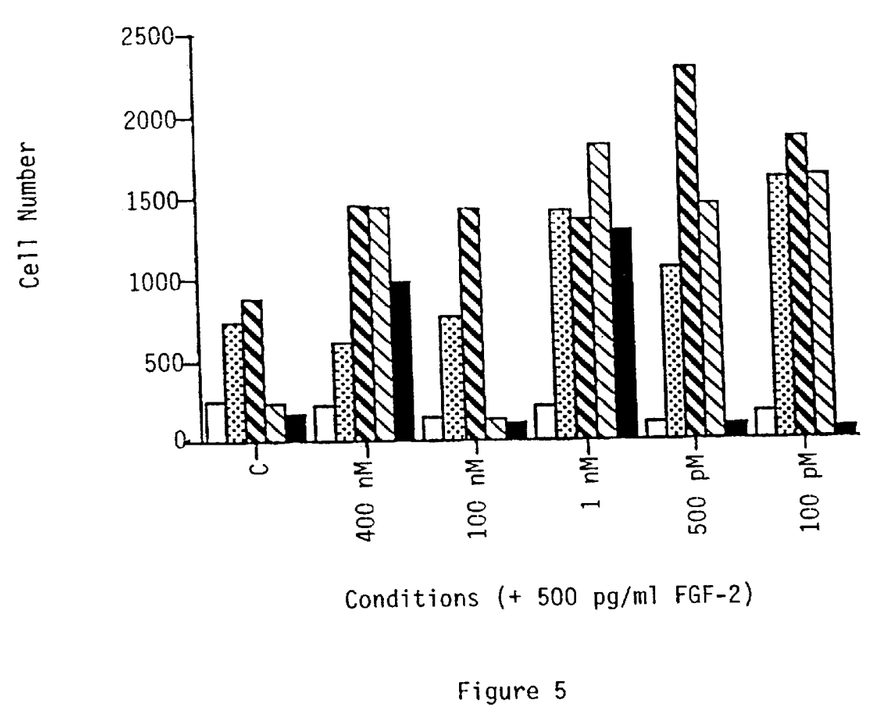
FIG. 5 is a graph of the effects of Ribavirin on HCN cells (at plating density of 25,000 cells/well) in the presence of FGF-2. Cell numbers on Day 0 are represented by open boxes; cell numbers on Day 1 are represented by spotted boxes; cell numbers on Day 3 are represented by darkly hatched boxes; cell numbers on Day 5 are represented by lightly hatched boxes; and cell numbers on Day 7 are represented by blackened boxes.

As can be seen in FIGS. 4 and 5, Ribavirin augmented/ enhanced FGF-2 actions. Ribavirin's effects were more pronounced at lower concentrations, i.e., less than about 1 nM. The proliferative effects are most pronounced at day 1. The survival effect is evident through the 7-day period.

The effect of Ribavirin on FGF-2 induced neurite elongation can be seen in photographs of HCN cells exposed to FGF-2 and varying concentrations of Ribavirin (A—control, no Ribavirin; B—400 nM Ribavirin; C—100 nM Ribavirin; D—1 nM Ribavirin; E—0.5 nM Ribavirin; and F—0.1 nM Ribavirin). At all Ribavirin concentrations tested there is increased elongation and networking of the neurites.

Effect on Non-neuronal Cells

Fibroblasts and astrocytes were subject to the same experimental condition as the PC12 and HCN cells. Unlike the neuronal cell lines, Ribavirin was without effect.

In all cell lines, both neuronal and non-neuronal, Ribavirin was toxic at concentrations greater than about 400 nM. The toxic effect of Ribavirin can be seen in photographs of HCN cells exposed to varying concentrations of Ribavirin (control, no Ribavirin; 400 nM Ribavirin; 800 nM Ribavirin; 1000 nM Ribavirin) where the decrease in cell number is clearly visible at Ribavirin concentrations of 800 nM and 1000 nM.

EXAMPLE 5

In Vivo Stimulation of Neurons by Ribavarin

Ribavirin was directly infused into the peritoneal cavity. After a survival period, the animals were tested for behavioral improvements and were then sacrificed and their brains analyzed. The brain was removed and placed on dry ice and analyzed for anatomical changes.

Direct Infusion into Ventricle. Ribavirin is directly infused into one of the lateral ventricles using stereotactic methods. The other ventricle serves as a control and receives an infusion of normal saline. Briefly, rats are anesthetized using sodium pentobarbital injected into the peritoneal cavity. Light anesthesia is maintained with ether during the Ribavirin injection. The scalp is pulled away exposing the skull. A hole is drilled in the skull using coordinates obtained from a stereotactic atlas. Ribavirin is infused at a rate of 1 $\mu$l/min. The animal is sacrificed one month later and the brain removed and placed on dry ice and analyzed for anatomical changes.

A. Model of Hunting's Disease

Rats are anesthetized with nembutal (25 mg/kg i.p) and injected with atropine sulfate (2 mg/kg i.p.). Animals sustain an ibotenate lesion of the striatum, simulating Huntington's Disease. 7 days after the lesion, the animals receive an injection of invention compositions under stereotaxic control. Injections are made to the lesioned area via a 21-gauge cannula fitted with a teflon catheter to a microinjector. Injected cells are labelled with fluorescein-labelled microspheres. Animals are given behavioral tests before the lesion, after the lesion, and at various intervals after transplantation with the microspheres to determine the functionality of the injected compositions at various postoperative time points. Animals are then perfused transcardially with 4% buffered parafornaldehyde, 0.1% glutaraldehyde and 5% sucrose solution at 4° C., and the brains are processed using standard anatomical techniques and analyzed.

B. Parkinson's Disease

Two animal models of Parkinson's Disease are used. In the first model, unilateral dopamine neurons of the substantia nigra are lesioned by the stereotaxic administration of 6-OHDA into the substantia nigra in adult CD 1 and C57BL/6 mice, and Wistar rats. Mice are pretreated with desipramine (25 mg/Kg i.p.) and rats are pretreated with pargyline (50 mg/Kg i.p.) both of which prevent the action of 6-OHDA on noradrenergic neurons and allow the selective destruction of dopaminergic neurons. The second animal model used is the adult mutant Weaver mice (Jackson Labs, 3½ months), in which approximately 70% of the dopaminergic neurons of the substantia nigra are lost by the age of 3 months. Both animal models are anaesthetized and the compositions are injected into the striatal region of the animals according to the methods described above. The animals are allowed to survive for 15 days prior to sacrifice and the striatal tissue analyzed.

C. Cardiac Arrest

Transient forebrain ischemia is induced in adult Wistar rats by combining bilateral carotid occlusion with hypovolemic hypotension (Smith et al. (1984) Acta Neurol Scand 69:385–401). These procedures lesion the CA1 hippocampal pyramidal cells which is typical of damage observed in humans following cardiac arrest and the cause of severe memory and cognitive deficits. The compositions are introduced preferably into the lesioned hippocampal of the ischemia lesioned rats. After 8 days, the animals are sacrificed and their brains are removed and analyzed. After a survival period, the animals are tested for behavioral improvements and are then sacrificed and their brains analyzed.

D. Stroke

Occlusion of the carotid arteries precipitates the occurrence of ischemic damage similar to that which occurs during stroke. Adult Wistar rats, in which the middle cerebral artery has been occluded to produce symptomatic lesions in the caudal striatum and parietal cortex, are injected with invention compositions, preferably into the lesioned areas. After a survival period, the animals are tested for behavioral improvements and are then sacrificed and their brains analyzed.

E. Epilepsy

Implantation of an electrode into the amygdala is used to kindle the brain, inducing epileptic episodes and other symptoms of epilepsy. Invention compositions are injected into the rat, preferably into the hippocampal region. The animals are later tested for epileptic episodes and then sacrificed for analysis of the grafted tissue.

F. Alzheimer's Disease

Cognitive impairment is induced in rats and mice by ibotenic acid lesions of the nucleus basalis, or old animals, exhibiting signs of dementia, are used. Invention composition is introduced by injection into the mice, preferably into the frontal cortex, medial septal nucleus and the nucleus of the diagonal band of the brains of the animals. After a survival period, the animals are tested for cognitive ability and are then sacrificed to allow analysis of brain tissue.

G. Spinal Cord Injury and Disease

Spasticity is a debilitating motor disorder that is a common consequence of disorders such as spinal cord injury, MS, and cerebral palsy. Transection of the spinal cord is used to produce muscular paralysis and is followed by the development of spasticity, which is characterized by debilitating hyperactive tendon reflexes, clonus and muscle spasms. The composition is introduced by injection into the mice, preferably into the lumbar lateral funiculus. After a survival period, the animals are examined for improvement in motor control and are then sacrificed to allow for analysis of spinal tissue.

EXAMPLE 6

Water Maze Assays

Reports indicate old rodents learn in a water maze task (Gower and Lamberty, (1993) Behav. Brain. Res.

57:163–173). Animals with brain lesions have reduced ability to learn in a water maze task. Therefore, the water maze task was used to test the effects of Ribavirin on animals with brain lesions. Water maze acquisition and retention were tested as previously described (Kempermann et al., (1998) J. Neurosci. 18:3206–3212. ). Rodents from each group (naive animals; animals having brain lesions as described above and treated with Ribavirin and animals having brain lesions and treated with cytochrome C (cyto C), a protein with the approximate size and charge of nerve growth factor (NGF), a neurotropic factor), were tested with two trials per day over 10 days (blocks). The platform was hidden below the surface of the opaque water. The two starting points were changed daily. Each trial lasted either until the rodent had found the platform or for a maximum of 60 sec. All rodents were allowed to rest on the platform for 10 sec. Analyses of time to reach the platform (latency) were recorded semiautomatically by a video tracking system (San Diego Instruments). On day 11 a probe trial with the platform removed was performed and did not show differences among the groups.

Figure 6:
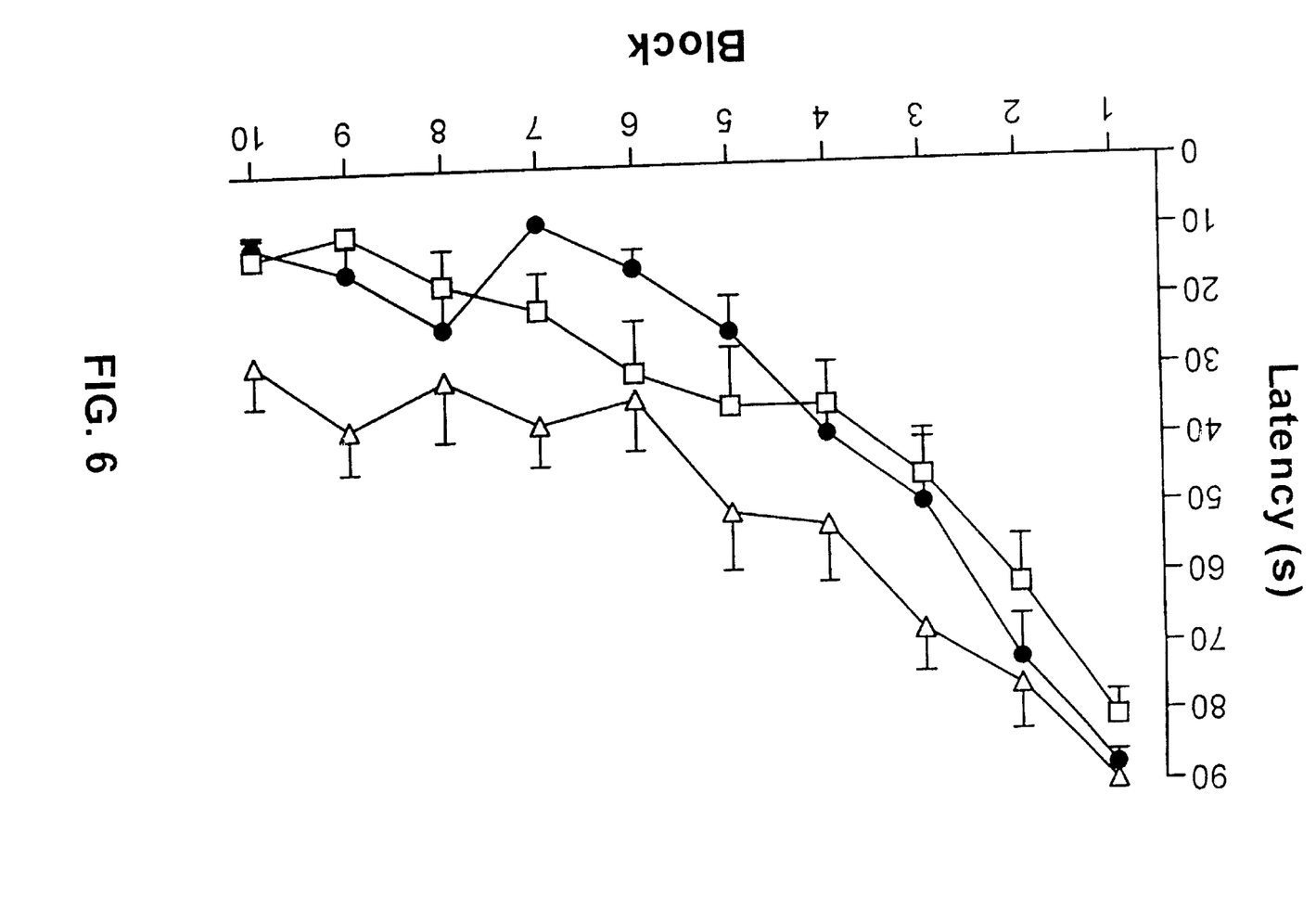
FIG. 6 shows the effects of Ribavirin on acquisition in a water maze assay. Data for each group of animals are as follows: Ribavirin-treated animals=●; naïve animals=□; Cyto C-treated animals=▽.
Figure 7A:
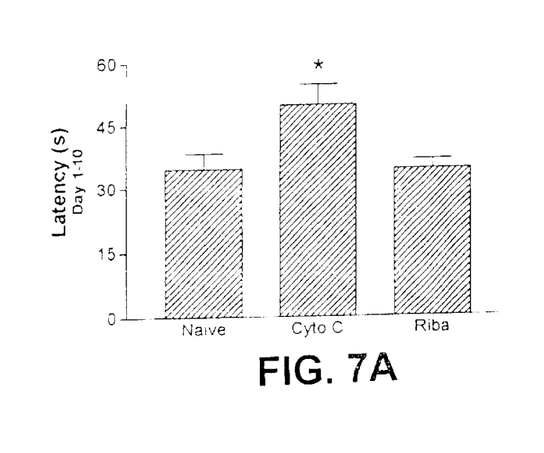
FIG. 7A relates to latency of acquisition in a water maze assay.
Figure 7B:
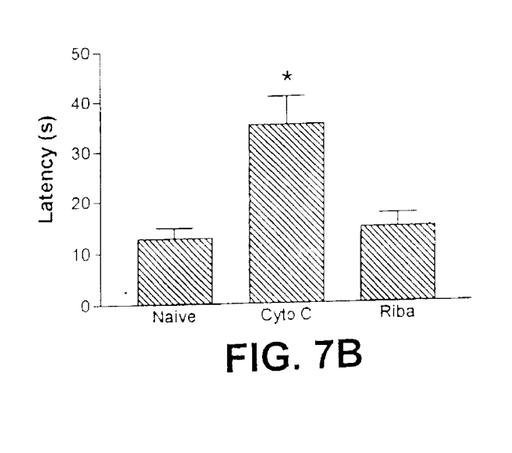
FIG. 7B relates to latency retention in a water maze assay.

Rodents in all groups demonstrate improved performances over the test period in a water maze acquisition assay. Overall analysis of time to reach the maze target revealed significant differences between control and treated animals. Rodents having brain lesions and treated with Ribavirin show a latency curve that is not statistically different from the latency curve of naive animals (FIG. 6). The mean latency is about 35 seconds for naive animals and for lesioned animals treated with Ribavirin, which is significantly different from the mean latency of about 50 seconds seen in animals treated with cyto C (FIG. 7A). In addition, the improved performance of each animal group as measured by the reduction in latency is retained (see FIG. 7B). Ribavirin-treated animals show retention of the learned latency of about 15 seconds which is not significantly different from the naive animal retained latency of about 13 seconds. Cyto C-treated animals show a retained latency of about 35 seconds, which is significantly different from the Ribavirin-treated animals.

A variation of the water maze test, a spatial probe test, was used to test the ability of animals to learn the location of a hidden platform. For this task, the escape platform was submersed under the opaque water surface in a fixed location, and rodents were given 24 trials over 4 consecutive days. The platform was kept in its lower position for the first 60 sec of the test and the search pattern was recorded. The platform was subsequently raised to its upper accessible position, after which the rodent usually found the platform. The rodents were released from the quadrant opposite to the platform on the probe test. The behavior of the rodents was tracked by computer, and analysis was accomplished off-line.

Figure 7C:
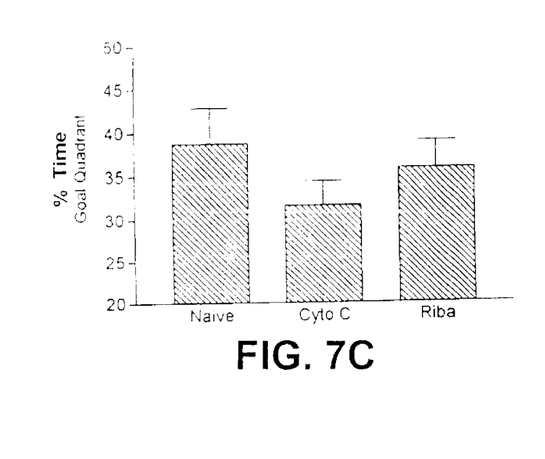
FIGS. 7C and 7D relate to a spatial probe variant of the water maze assay.
Figure 7D:
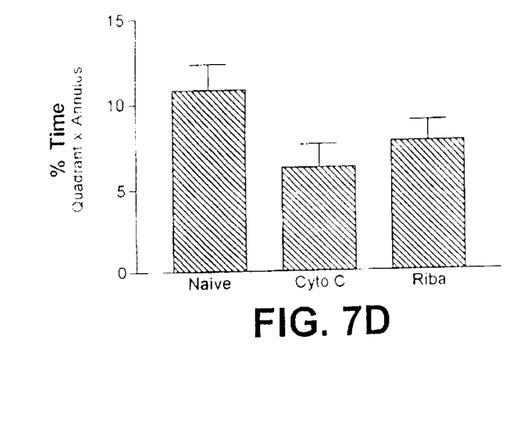

Naïve rodents spend about 38% of the time in the goal quadrant where the platform is located and lesioned rodents treated with Ribavirin spend about 36% in the goal quadrant. In contrast, rodents treated with cyto C spend significatnly less time, (i.e., about 32% of the time) in the goal quadrant (FIG. 7C). A similar pattern is seen amongst animals when time spent at the hidden platform is assessed (FIG. 7D.).

This study demonstrates that treatment with Ribavirin can decrease the latency of acquisition in behavioral tasks in rodents with brain lesions. Lesioned animals treated with Ribavirin retain the decreased latency over time. In addition, lesioned animals treated with Ribavirin appear to perform more rapidly in a spatial probe assay.

EXAMPLE 6

Growth Cone Studies

The ability of compounds to stimulate neurite elongation as determined by growth cone turning was evaluated in vitro. PC 12 cells were cultured as described above (see Example 1). Cells growing in culture were exposed to a focal site of Ribavirin and control compounds and the number of growth cones with a turning angle was measured and the turned angle of each growth cone was measured. Ribavirin stimulated growth cone turning (FIGS. 8C and 8D) compared to control substances (FIGS. 8A–8B).

Figure 8:
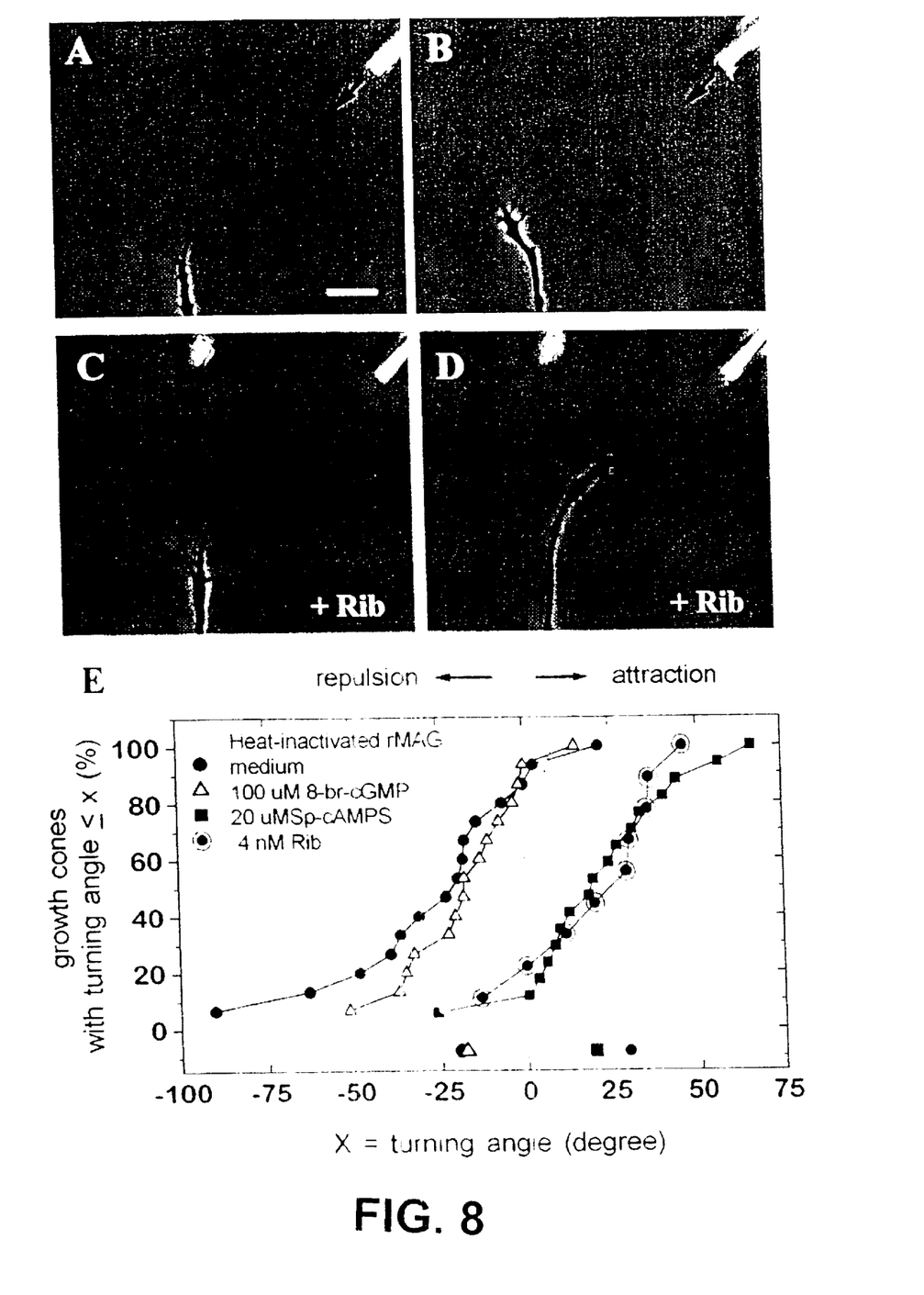

PC12 cells grown as described above showed increased turning towards the Ribavirin site (attraction) as compared with cells encountering control compounds which show turning away from the site (i.e., repulsion; medium 8-bromo-cGMP) or no turning (heat inactivated rMAG (recombinant myelin associated glycoprotein)) (FIG. 8E). Ribavirin is effective at concentrations in the nanomolar range.

These results demonstrate that Ribavirin has the ability to promote elongation of growth cones and influence the path taken by neurites during growth and development.

Enhancement of Neurotrophic Factors. The activity of neurotrophic factors, either endogenous or exogenous, is enhanced in the presence of Ribavirin and analogs thereof. When there is neurological disease or trauma, the oral administration of Ribavirin and analogs thereof provides a simple treatment that facilitates good compliance. Thus, the present invention provides a method to ameliorate the symptoms as well as treat the conditions of neurological disease and/or trauma. Cell survival and enhanced recovery are assessed by behavioral measures and electrophysiology.

While the invention has been described in terms of various preferred embodiments, the skilled artisan will appreciate that various modifications, substitutions, omissions and changes may be made without departing from the scope thereof. Accordingly, it is intended that the scope of the present invention be limited solely by the scope of the following claims, including equivalents thereof.

What is claimed is:

1. A pharmaceutical composition comprising:
   i) a 1-(β-D)ribofuranosyl)-1H-1,2,4-triazole compound; and
   ii) a neurotrophic factor.

2. A pharmaceutical composition according to claim 1 wherein the triazole compound is of the structure wherein R is selected from the group consisting of carboxamide, carboxamidine, and thiocarboxamide; and wherein X is selected from the group consisting of hydrogen, phosphate, and $C_1$–$C_{18}$ acyl.

3. A pharmaceutical composition according to claim 1 wherein the triazole compound is 1-(β-D-ribofuranosyl)-1H-1,2,4-triazole3-carboxamide.

4. A pharmaceutical composition according to claim 1 wherein the triazole compound is 1-(5'-O-butyryl-β-D-ribofuranosyl)-1H-1,2,4-triazole3-carboxamide.

5. A pharmaceutical composition according to claim 1 wherein the triazole compound is 1-(5'-O-phosphate-β-D-ribofuiranosyl)-1H-1,2,4-triazole-3-carboxamide.

6. A pharmaceutical composition according to claim 1 wherein the triazole compound is 1(2',3',5'-O-acetyl-β-D-ribofuranosyl)1H-1,2,4-triazole-3-carboxamide.

7. A pharmaceutical composition according to claim 1 wherein the triazole compound is 1-(β-D-ribofuranosyl)-1H-1,2,4-triazole-3-carboxamidine.

8. A pharmaceutical composition according to claim 1 wherein the neurotrophic factor is selected from the group consisting of NGF, FGF, BDNF, NT-3, GDNF and CNTF.

9. A composition comprising.
   i) a 1-(β-D-ribofuiranosyl)-1H-1,2,4-triazole compound;
   ii) a neurotrophic factor; and
   iii) a pharmaceutically acceptable carrier.

10. A method of enhancing neurite outgrowth, neuronal survival and neuronal proliferation in a mammalian cell, said method comprising administering to said cell an effective amount of a composition comprising:
    i) a 1-(β-D-ribofuranosyl)-1H-1,2,4triazole compound; and
    ii) a neurotrophic factor.

11. The method of claim 10 wherein the administration is in vitro.

12. The method of claim 10 wherein the administration is in vivo.

13. The method of claim 10 wherein the administration is to a mammal.

14. The method of claim 10 wherein the triazole compound is of the structure wherein R is selected from the group consisting of carboxamide, carboxamidine, and thiocarboxamide; and wherein X is hydrogen, or $C_1$–$C_{18}$ acyl.

15. The method according to claim 10 wherein the triazole compound is 1-(β-D-ribofuiranosyl)-1H-1,2,4-triazole-3-carboxamide.

16. The method according to claim 10 wherein the triazole compound is 1-(5'-O-butyryl-β-D-ribofuranosyl)-1H-1,2,4triazole-3-carboxamide.

17. The method according to claim 10 wherein the triazole compound is 1-(5'-O-phosphate-β-D-ribofuranosyl)-1H-1,2,4-triazole-3-carboxamide.

18. The method according to claim 10 wherein the triazole compound is 1-(2',3',5'-O-acetyl-β-D-ribofuranosyl)-1H-1,2,4-triazole-3-carboxamide.

19. The method according to claim 10 wherein the triazole compound is 1-(β-D-ribofuiranosyl)-1H-1,2,4-triazole-3-carboxamidine.

20. The method according to claim 10 wherein the neurotrophic factor is selected from the group consisting of NGF, FGF, BDNF, NT-3, GDNF and CNTF.

* * * * *